(12) United States Patent
Maewal

(10) Patent No.: US 9,308,223 B2
(45) Date of Patent: *Apr. 12, 2016

(54) OM VITAMIN FORMULA

(71) Applicant: Renuka Maewal, Fort Worth, TX (US)

(72) Inventor: Renuka Maewal, Fort Worth, TX (US)

( * ) Notice: Subject to any disclaimer, the term of this patent is extended or adjusted under 35 U.S.C. 154(b) by 122 days.

This patent is subject to a terminal disclaimer.

(21) Appl. No.: 13/987,329

(22) Filed: Jul. 15, 2013

(65) Prior Publication Data

US 2014/0348949 A1 Nov. 27, 2014

Related U.S. Application Data

(63) Continuation-in-part of application No. 12/220,339, filed on Jul. 24, 2008, now Pat. No. 8,440,243.

(51) Int. Cl.
| | |
|---|---|
| A61K 8/67 | (2006.01) |
| A61K 33/26 | (2006.01) |
| A61K 31/525 | (2006.01) |
| A61K 31/51 | (2006.01) |
| A61K 31/455 | (2006.01) |
| A61K 31/4415 | (2006.01) |
| A61K 31/714 | (2006.01) |
| A61K 31/197 | (2006.01) |
| A61K 31/519 | (2006.01) |
| A61K 31/015 | (2006.01) |
| A61K 31/4188 | (2006.01) |
| A61K 31/14 | (2006.01) |
| A61K 31/07 | (2006.01) |
| A61K 31/355 | (2006.01) |
| A61K 45/06 | (2006.01) |
| A61K 31/375 | (2006.01) |
| A61K 31/445 | (2006.01) |

(52) U.S. Cl.
CPC . *A61K 33/26* (2013.01); *A61K 8/67* (2013.01); *A61K 31/015* (2013.01); *A61K 31/07* (2013.01); *A61K 31/14* (2013.01); *A61K 31/197* (2013.01); *A61K 31/355* (2013.01); *A61K 31/375* (2013.01); *A61K 31/4188* (2013.01); *A61K 31/445* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/714* (2013.01); *A61K 45/06* (2013.01)

(58) Field of Classification Search
USPC .............................. 426/73; 514/52; 424/1.73
See application file for complete search history.

(56) References Cited

U.S. PATENT DOCUMENTS

| | | | | |
|---|---|---|---|---|
| 5,405,613 | A | * | 4/1995 | Rowland ..................... 424/439 |
| 8,440,243 | B2 | * | 5/2013 | Maewal ........................ 426/73 |
| 2006/0153912 | A1 | * | 7/2006 | Habich et al. ................. 424/464 |

* cited by examiner

*Primary Examiner* — Ali Soroush

(57) ABSTRACT

A composition comprising various vitamins to make a multi-vitamin. The vitamins identified in multi-vitamin include vitamin B-1, vitamin B-2, niacinamide, vitamin B-6, vitamin B-12, pantothenic acid, folic acid, beta carotene, iron, biotin, choline, vitamin A, vitamin E and vitamin C. The multi-vitamin soothe pain, depression, weakness and insomnia and works best with variety of food and less dairy products. Lead combined with calcium effects are severe than lead effects only; it elevates blood pressure, cholesterol, glucose, weight and cause frequent infections; bigger than normal dose of antibiotics need in infections; and variation in quantities of vitamins are needed to soothe the symptoms.

3 Claims, No Drawings

OM VITAMIN FORMULA

This specification is continuation in part of application Ser. No. 12/220,339 filed on Jul. 24, 2008 and U.S. Pat. No. 8,440,243 B2 issued on May 14, 2013. Vitamin performance has enhanced since and some details left to be disclosed previously are disclosed now. Vitamin quantities are clarified for Lead intoxication only and Lead intoxication combined with some other health conditions—infection, bleeding and elevated sugar. Especially, optimum quantity of beta carotene is described for Lead intoxication with or without other health issues. Further, vitamin quantities are added for Lead intoxication combined with calcium effects.

BACKGROUND OF THE INVENTION

I had intoxicated Lead from tap water. I had severe ill-health symptoms: pain, itching, burning, insomnia, depression, panic attacks. I went through tremendous suffering for years because of the Lead intoxication. I have treated my ill-health symptoms by taking variety of vitamins in varying dose and came up with the vitamin formula. Therefore, I have invented a vitamin formula named as "OM VITAMIN FORMULA" that will alleviate ill-health symptoms of Lead intoxication. People are intoxicating Lead knowingly or unknowingly from tap water or by some other means. Many of us are not aware of Lead effects on body from tap water. As a result of Lead intoxication body cells have ongoing damage, and the requirement of vitamins increases in a specific way, and there is no way to feel right in the absence of vitamins. I have a very high confidence level that this formula can help many all around the world for ill-health symptoms especially induced by Lead without a disease.

Further, intake of dairy products prevents Lead depleting from the body, exact mechanism is not known but it happened in my case. It is quite simple that Lead intoxication compounds with milk products (Calcium) in body and produces additional symptoms: obesity, elevated blood sugar level, elevated blood pressure, elevated cholesterol and frequent infections.

My blood Lead level was 7 Mg/dl which is considered normal according to Occupational Safety and Health Administration (OSHA)'s guidelines. I was exposing to a Lead level of 3.6 to 14 ppb in my house. But after going through all of the suffering, I think lower Lead level for longer time can produce Lead poisoning in body without elevating the blood Lead level. I believe blood Lead level shows what a person is exposed to and not the actual Lead deposited into the body. Further, the blood Lead level limit of 15 Mg/dl, considered harmful, as published in OSHA's guidelines needs to be reviewed. In my case blood Lead level was lower than 15 Mg/dl but my body had sufficient amount of Lead. I have researched the Lead intoxication effects and cure fully; some measures from OSHA or other agencies deem necessary to safeguard us from harm.

BRIEF SUMMARY OF THE INVENTION

I have invented a vitamin formula that will alleviate the ill-health symptoms induced by Lead intoxication from tap water or by some other means. Ill-health symptoms are: pain, itching, burning, insomnia, depression, panic attacks, infections, elevated blood pressure, elevated cholesterol . . . . Also likely blood sugar level well be elevated. Lack of vitamins in presence of Lead will affect body growth and other body functions. As Lead increases the requirements of vitamins in body so body cells start becoming mega (bloated) which will result in weight gain. Further, blood test will not show high Lead level to treat because blood test only shows the Lead level a person is exposing to not severity of lead deposited into body system. Nowadays when causes for health problems are not known, this vitamin formula can become a blessing for all of us.

DETAILED DESCRIPTION OF THE INVENTION

I am born and grown up in India. I moved in a bigger than 5000 sqft house in 1987. I experienced excessive menstrual bleeding after moving in this house but problem was corrected in 1988 by laser surgery. I started having ill-health symptoms in 1990. I was slow and sluggish. I had some muscle and joint pain, for example, if I would hold a purse, my wrist and arm muscle would hurt. My neck and shoulder joints were hurting more than any other part of the body. I had lot of stiffness in my back and I used to get nervous quite often. I went to a doctor. He ran some blood test and said my sedimentation rate was not right, probably low. And he couldn't see anything wrong in me to treat. I came home and went through suffering. However, I started taking a multi-vitamin tablet with some iron and milk. I felt better but not quite right.

This went for 5 to 6 months, then suddenly I started having mood swings. I was sitting quietly for hours. As this was not my normal personality, I started thinking what is going wrong. Further, I felt a kind of whirling motion in the roots of my hairs on extremities of my neck. It appeared like tiny bugs were crawling on my head. I became worried about my routine chores. Six more months passed by, more symptoms were showing up. I was very cold and shivering. I had lot of pain and numbness in my legs. I felt very weak. This gave me an indication of being anemic. I had blurry and watery eyes. My body and face gave the appearance of shrinking and bloating intermittently. I was amazed. I brought some B-Complex and Iron and started taking them regularly.

I was frighten inside and was sure that something was going wrong inside my body. I went to see the doctor again. He ran some blood tests and said results looked normal regardless of vitamins I was taking to alleviate ill-health symptoms.

As the time went by, I was becoming weaker everyday and my vitamins dose was increasing. This did not seem right so I decided to see some other doctor, Dr. D. As usual he ran some blood test and found nothing wrong. It was January 1992. I was unable to sleep, my nerves and muscles would pull during work. I was depressed most of the time. I went to Dr. D again. Nothing happened. I came back with a prescription for depression medicine. I was told, take it at night, and I will be okay in the morning.

I was not satisfied. My inner voice said to me that this was absolutely wrong. I am in real suffering and pain, and something terrible is going wrong inside my body. If a doctor fails to identify the problem, then he or she should not prescribe any medication. I had no choice but to become my own doctor. I stayed on moderate dose of B-Complex and iron without knowing the cause of my discomfort. I had no idea if I was doing right or wrong, only a moderate dose of vitamins gave me a normal healthy feeling.

But this did not last longer, more severe symptoms started showing up. At this point I should say that anyone with these mediocre Lead-induced symptoms can be cured without any medical help simply by removing the cause. A moderate dose of vitamins may be needed depending on the severity of the symptoms.

It was June 1992. In addition to all these symptoms as described earlier, I had lot of stiffness in my abdominal area. My White Blood Cell (WBC) count was 9.3. I used to look pale. I was having panic attacks. I was still on moderate dose of vitamins because whenever I stopped it, I felt very weak. Inflammation started spreading in my body. One night it was so severe that I couldn't sleep, so I went to emergency room. All they found high WBC, 11. Since there was no disease, there was no medical help.

Symptoms were getting worst, I went to see a neurologist. He noticed high WBC, 12.6, and recommended to see a infectious disease doctor. As usual he couldn't see anything wrong. It was at the end of October 1992.

I was in a severe suffering condition with no sleep and peace. As I was going to work, I had the realization that I felt better at work and once I came home, I felt worse. One day I came home from work and had a very severe panic attack, like my heart almost failed to pump. I had a near death experience. I assumed right away that Lead in water is causing health problems. It was November 1992. I stopped drinking tap water. There was some relief, but all suffering and pain was with me.

I was already taking vitamins, so I started working with variety of vitamins in varying doses to alleviate the suffering. This was like an experiment on my body to find a balanced dose to alleviate Lead intoxication symptoms. It took me one and half decade to find the correct mix and proportion of vitamins. I will explain later why it took me so many years.

Vitamins dose was working correctly, however, I was taking certain quantity of milk (Calcium) in my diet so dose was adjusted with certain quantity of milk also. And I believe higher quantity of Calcium did not let Lead released from my body, exact mechanism is not known. However, most of the symptoms as described earlier were alleviated with vitamins. In 2001, dizziness was extreme and glucose test was very close to borderline. Additional symptoms like some weight gain, elevated blood pressure and elevated cholesterol were noted. I realized immediately that I have done something wrong in working out the vitamin dose for Lead intoxication so I reversed engineering to figure out the dose with less quantity of milk. In 2005-2006 timeframe, I started gaining confidence that vitamin dose to cure Lead intoxication is absolutely correct and I decided to file the patent papers. I do not want to die taking a vast amount of knowledge and cure for Lead intoxication with me. I wish I could have this dose in 1990 then I didn't have to go through all the suffering and pain from 1990-2005, almost fifteen years. Therefore the vitamin dose or multi-vitamin formula for Lead intoxication is determined by trial and error method and is the result of fifteen years of work. Sometimes God makes the things happen for purpose and I was chosen the vehicle.

While I was figuring out the vitamin formula for Lead intoxication, I was experiencing on and off the following health symptoms:

Allergy, stuffy nose, blurring and watery eyes, muscles and joint pain, burning and itching, upset stomach, stress, occasional mercy breath, sleep disturbances, violent mood, anger, dizziness, depression, panic attacks, anxiety, fatigue, nervousness, confusion, disorientation, and infection.

All these symptoms depend upon the amount of lead in body and the kind of diet and vitamins I was taking. I went through lot of ups and downs in figuring out the vitamin dose or formula to cure Lead induced ill-health symptoms. I gained so much experience by working trial and error methods on vitamins that I could simulate most of these symptoms in my body. I called this formula, OM VITAMIN FORMULA. Om is the first name of my mother and unfortunately she was in USA with me in 1992 when I was desperate to find out the cause for my suffering and pain. I have shown this formula below as OM-50 dose, primarily because some vitamins' quantities are in 50 unit. Multiply all the ingredients by 2 will give OM-100, and divide by 2 will give OM-25, and so on.

OM Vitamin Formula

|  | OM-50 |
|---|---|
| B-1(Thiamine)(mg) | 50 |
| B-2(Riboflavin)(mg) | 12.5 |
| Niacinamide(mg) | 50 |
| B-6(Pyridoxin)(mg) | 20 |
| B-12(Cyanocobalamin)(mcg) | 50 |
| Pantothenic Acid(mg) | 55 |
| Folic Acid(mcg) | 15 |
| Beta Carotene(I.U.) | 18,000-30,000 |
| Iron(mg) | 50 |
| Biotin(mcg) | 20 |
| Choline(mg) | 30 |
| Vitamin A(I.U.) | 8,000 |
| Vitamin E(I.U.) | 100-200 |
| Vitamin C(mg) | 350 |

OM VITAMIN FORMULA will work for Lead intoxication and Lead intoxication combined with some other health conditions. It turned out a simple basic formula. Variation in quantities of beta carotene and vitamin E is required during infection, bleeding and elevated sugar level. Lower quantities of beta Carotene and vitamin E are good for Lead only and Lead plus infection; higher quantities of beta Carotene and vitamin E work quite well for Lead plus bleeding and/or Lead plus elevated sugar. Beta Carotene quantity around 20,000 I.U. and vitamin E quantity around 100 I.U. soothe very effectively Lead intoxication symptoms with no other health conditions. Beta Carotene quantity greater than 20,000 I.U. is good for Lead intoxication plus bleeding and/or Lead intoxication plus elevated sugar. Requirement of vitamin E goes up during Lead intoxication plus bleeding and/or Lead intoxication plus elevated sugar. Beta Carotene quantity is slightly lower in infection than Beta Carotene quantity in Lead intoxication only; therefore, low value of beta Carotene is shown 18,000 I.U. Beta Carotene 30,000 I.U. was very effective during heavy bleeding and/or elevated sugar level. Beta Carotene quantity went up to 40,000 I.U. and higher in presence of severe bleeding and/or high sugar level.

Further if Lead intoxication has compounded with milk (calcium) as I mentioned previously then adjustment have to be made in quantities of the vitamins. Most manipulation was done in quantities of B-2, B-6, folic acid and beta carotene. Optimum quantities of vitamins in Lead intoxication compounded with calcium:

| B-1(Thiamine)(mg) | 100-200 |
|---|---|
| B-2(Riboflavin)(mg) | 100-200 |
| Niacinamide(mg) | 100-200 |
| B-6(Pyridoxin)(mg) | 18-52 |
| B-12(Cyanocobalamin)(mcg) | 100-200 |
| Pantothenic Acid(mg) | 110-220 |
| Folic Acid(mcg) | 400-600 |
| Beta Carotene(I.U.) | 12,800-22,500 |
| Iron(mg) | 100-200 |
| Biotin(mcg) | 20-40 |
| Choline(mg) | 30 |
| Vitamin A(I.U.) | 8,000-12,000 |

-continued

| | |
|---|---|
| Vitamin E(I.U.) | 100-200 |
| Vitamin C(mg) | 350 |

Big dose of multi-vitamin is needed in case of Lead intoxication compounded with calcium. Higher quantities of vitamins apply to chronic Lead combined with calcium effects; with low intake of dairy products, excess calcium flushes out and then lower quantities will work. Calcium depletes from the body much faster than Lead does so once calcium goes out of the body then OM formula shown above will work effectively. Also, bigger than normal dose of antibiotics is required to treat infections if Lead intoxication has compounded with calcium. I had to take anywhere from 25% to 50% bigger than normal dose of antibiotics during infections. I have data on how the vitamins varied when Lead intoxication was compounded with milk (calcium) in 2002-2007 timeframe. However, complete cure comes only after Lead depletes from the body.

By taking the vitamins, I felt normal most of the time. Obvious effects of not taking the vitamins: Weight Gain, Double Chin Appearance (only if Lead exposure is higher), Frequent Infections, Allergy, Elevated Blood Pressure, Elevated Blood Sugar, Elevated Cholesterol Pain, Depression, Insomnia and much more. Presence of lead in body increases the requirement of vitamins and lack of vitamins will affect body growth, menstrual bleeding (elevated) and other body functions.

My blood Lead level was 7 Mg/dl which is considered normal according to Occupational Safety and Health Administration (OSHA)'s guidelines. I was exposing to a Lead level of 3.6 to 14 ppb in my house. But after going through all of this, I think lower Lead level for longer time can produce Lead poisoning in body without elevating the blood lead level. I believe blood lead level shows the Lead level a person is exposed to and not the actual Lead deposit into the body. Further, the blood lead level limit of 15 Mg/dl, considered harmful, as published in OSHA's guidelines needs to be reviewed. In my case blood lead level was lower than 15 Mg/dl but my body had sufficient amount of Lead. I have researched the Lead intoxication effects and cure fully; some measure from OSHA or other agencies deem necessary to safeguard us from harm.

I have written a small book "Lead Syndrome" in 1996 to educate others on how we can suffer lifelong from Lead intoxication from household tap water. But unfortunately, word did not get through. I titled this book Lead Syndrome because blood Lead level would not cross the limit 15 Mg/dl, high enough to be categorized as Lead Poisoning. I was not aware that my Lead intoxication problem had been compounding with milk (calcium) when I had written the book in 1996. However, the book depicts ill-health symptoms of Lead intoxication and also ill-health symptoms of Lead intoxication compounded with milk (calcium). This book has my real life suffering data, experience, analysis and results. I can provide hard copies of this book at request. The combined effects of Lead and Calcium are quite disastrous to health and require a big dose of multi-vitamin and folic acid to alleviate the suffering. Multi-vitamins off the shelf did not help me in my suffering because so far vitamins are not made by practically assessing on how body requirement for vitamins changes after exposing to foreign materials, Lead in my case.

Last but not least, I believe that combined effect of Lead intoxication and Dairy products on health are worse than the effect of Lead intoxication only, and these are likely the primary contributor to ill-health and precursor for major diseases. Many of us will fall in this category as Lead is going in body unknowingly and dairy products are going in body knowingly. So consequences are lifelong ill-health and unbearable suffering. I suffered a lot but I gained a lot in working out solution to resolve my health dilemma. Not only this, my observation reveals that parents are in better health than children that is particularly alarming.

The invention claimed is:

1. A multi-vitamin supplement to soothe lead intoxication symptoms with health conditions, the supplement consists of: 50 mg of B-1 (thiamine), 12.5 mg of B-2 (riboflavin), 50 mg of niacinamide, 20 mg of B-6 (pyridoxin), 50 mcg of B-12 (cyanocobalamin), 55 mg of pantothenic acid, 15 mcg of folic acid, 18,000-30,000 I.U. of beta carotene, 50 mg of iron, 20 mcg of biotin, 30 mg of choline, 8,000 I.U. of vitamin A, 100-200 I.U. of vitamin E, and 350 mg of vitamin C.

2. A multi-vitamin supplement to soothe lead intoxication symptoms with no health conditions, the supplement consists of: 50 mg of B-1 (thiamine), 12.5 mg of B-2 (riboflavin), 50 mg of niacinamide, 20 mg of B-6 (pyridoxin), 50 mcg of B-12 (cyanocobalamin), 55 mg of pantothenic acid, 15 mcg of folic acid, 20,000 I.U. of beta carotene, 50 mg of iron, 20 mcg of biotin, 30 mg of choline, 8,000 I.U. of vitamin A, 100 I.U. of vitamin E, and 350 mg of vitamin C.

3. A multi-vitamin supplement to soothe lead intoxication symptoms compounded with calcium, the supplement consists of: 100-200 mg of B-1 (thiamine), 100-200 mg of B-2 (riboflavin), 100-200 mg of niacinamide, 18-52 mg of B-6 (pyridoxin), 100-200 mcg of B-12 (cyanocobalamin), 110-220 mg of pantothenic acid, 400-600 mcg of folic acid, 12,800-22,500 I.U. of beta carotene, 100-200 mg of iron, 20-40 mcg of biotin, 30 mg of choline, 8,000-12,000 I.U. of vitamin A, 100-200 I.U. of vitamin E, and 350 mg of vitamin C.

* * * * *